United States Patent [19]

Breslow et al.

[11] Patent Number: 5,272,166
[45] Date of Patent: Dec. 21, 1993

[54] METHOD FOR SELECTIVE REDUCTION OF LP(A)

[75] Inventors: Jan L. Breslow, Scarsdale; Dov Gavish, New York, both of N.Y.

[73] Assignee: The Rockefeller University, New York, N.Y.

[21] Appl. No.: 844,903

[22] Filed: Mar. 2, 1992

Related U.S. Application Data

[63] Continuation of Ser. No. 506,868, Apr. 9, 1990, abandoned.

[51] Int. Cl.$^5$ ............... A61K 31/415; A61K 31/195; A61K 31/19; A61K 31/095
[52] U.S. Cl. ................................. 514/390; 514/562; 514/574; 514/706; 514/948; 424/439; 424/440
[58] Field of Search ............... 514/390, 562, 574, 706, 514/948; 424/439, 440

[56] References Cited

FOREIGN PATENT DOCUMENTS 318773   11/1981   European Pat. Off. .
132956   7/1985    Japan .
880615   1/1988    Japan .
5701968  6/1971    United Kingdom .
2729273  12/1975   United Kingdom .
7912677  11/1980   United Kingdom .

OTHER PUBLICATIONS (Author Unknown) Opportunities in Biology, National Research Counsel (pp. 328-334), (1978).
Armstrong, Victor W., et al., "Isolation, characterization, and uptake in human fibroblasts of an apo(a)-free lipoprotein obtained on reduction of lipoprotein(a)" J. Lipid Res. 26:1314-1323 (1985).
Eldeib, M. M. R., et al., "Reversal of the Biological Activity of Escherichia coli Hear-Stable Enterotoxin by Dusulfide-reducing Agent Infection & Immunity" 51(1):24-30 (Jan., 1986).
Bihari-Varga, M., et al. "Interaction of Lippoprotein Lp(a) and Low Density Lipoprotein with Glycosaminoglycans from Human Aorta". Arteriosclerosis 8(6):851-857 (Nov.-Dec. 1988).
Reynolds, J.(ed) Martindale The Extra Pharmacopoeid (29th ed) (1989). Copies of the pages submitted herewith relate generally to sulfhydryl group reducing agents.
Dictionnaire Vidal (1989) contains a monograph in French pertaining to the commercially available product MUCOMYST. While a translation of this monograph has not been obtained, but a copy of the MUCOMYST product brochure which has been circulated in the United States is enclosed.
Hajjar, K. A., et al., "Lipoprotein (a) modulation of endothelial cell surface fibrinolysis and its potential role in atherosclerosis" Nature 339(6222):303-305 (May 25, 1989).
Kostner, Gerhard M., et al., "HMG CoA Reductase Inhibitors Lower LDL Cholesterol Without Reducing Lp(a) Levels" Circulation 80(5):1313-1319 Nov. 1989.
Utermann, G. "The Mysteries of Lipoprotein (a)" Science 246:904-910 (Nov. 17, 1989).
Gavish, D., et al., "Plasma Lp(a) Concentration is Inversely Correlated with the Ratio of Kringle IV/Kringle v Encoding Domains in the Apo(a) Gene" J. Clin Invest. 84:2021-2027 (Dec. 1989).
Gavish, D., et al., "Lipoprotein(a) reduction by N-acetylcysteine" The Lancet 337(8735):203-204 (Jan. 26, 1991).
Stalenhoef, A., "N-acetylcysteine and lipoprotein": The Lancet 337(8739):491 (Feb. 23, 1991).
Hansen, P. R., "Lipoprotein(a) reduction by N-acetylcysteine" The Lancet 337(8742):672-673 (Mar. 16, 1991).
Chemical Abstracts (106: 101184a) 1987.
Chemical Abstracts (107: 114684j) 1987.

Primary Examiner—Frederick E. Waddell
Assistant Examiner—K. Weddington
Attorney, Agent, or Firm—Klauber & Jackson

[57] ABSTRACT

The present invention relates to methods and corresponding agents for lowering plasma Lp(a) levels by the administration of agents that reduce Lp(a) and selectively separate therefrom the apo(a) component and/or prevent Lp(a) formation. Suitable agents include sulfhydryl reducers, such as N-acetylcysteine. The present method and agents may be administered alone or in conjunction with other therapy for the lowering of LDL cholesterol.

24 Claims, 2 Drawing Sheets

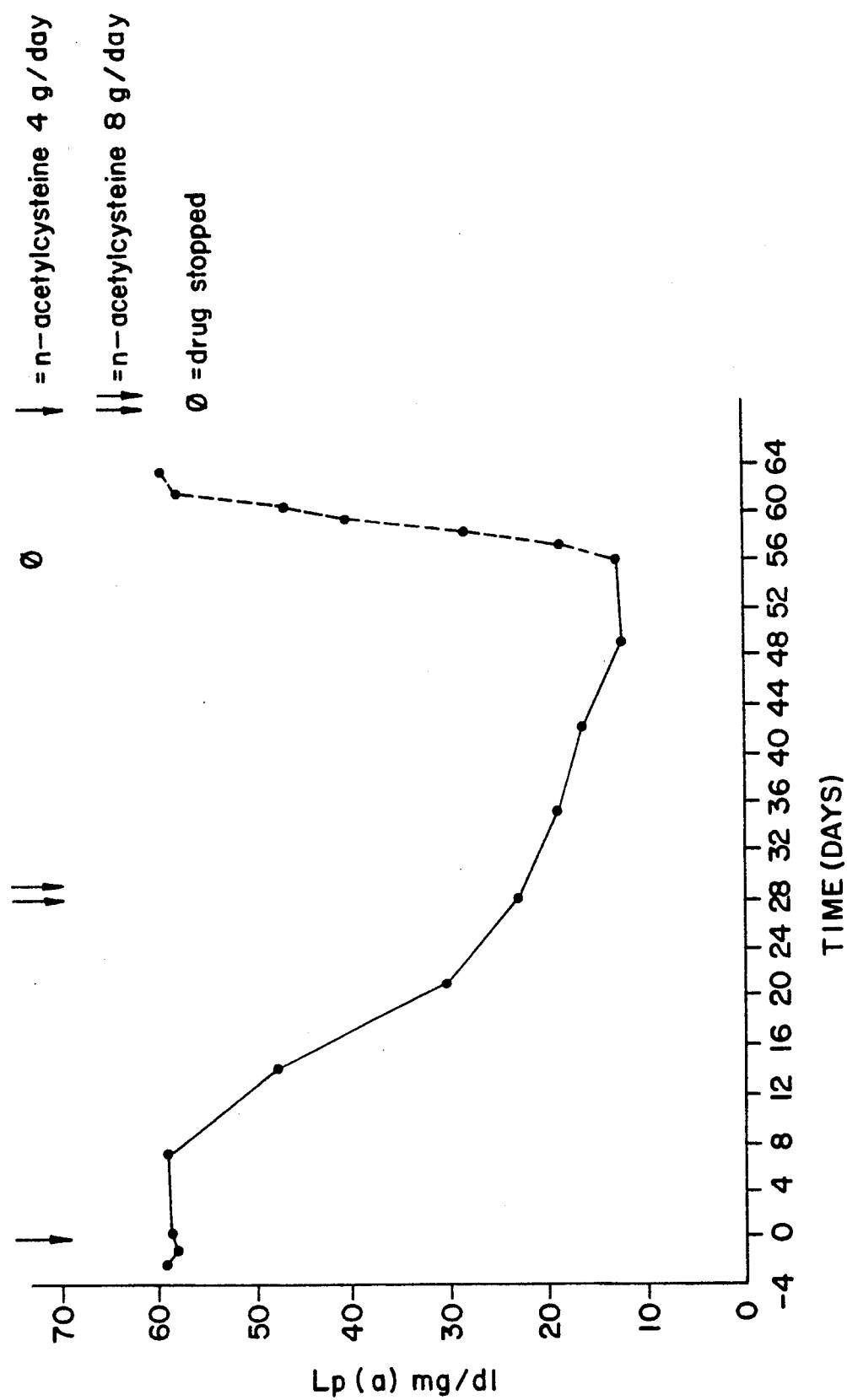

METHOD FOR SELECTIVE REDUCTION OF LP(A)

This invention was made with Government support under Grants HL-32435 and HL-36461 awarded by the National Institutes of Health. The Government may have certain rights in the invention.

CROSS REFERENCE TO RELATED APPLICATIONS

This application is a continuation of U.S. application Ser. No. 07/506,868 filed Apr. 9, 1990 now abandoned, priority of which is claimed hereunder.

BACKGROUND OF THE INVENTION

The present invention relates generally to lipoprotein (a), Lp(a) and more particularly to methods and agents to lower its plasma concentrations to achieve therapeutic benefit.

The macromolecule known as lipoprotein (a) or Lp(a), is a complex of low density lipoproteins (LDL), and a hydrophilic glycoprotein that has been given the name apolipoprotein (a), or apo(a). The principal protein of LDL is apo B-100 and apo(a) is attached to the apo B moiety of LDL by a disulfide bond. LDL is the major transporter of cholesterol in human plasma. The physiological function of Lp(a) is unknown.

Apo(a) is not similar in structure to other apolipoproteins but exhibits similarity to another plasma protein called plasminogen. Plasminogen structure includes five tandemly repeated homologous domains called kringles (Kringles I-V), which are pretzel-like structures stabilized by three internal disulfide bridges followed by a protease domain. Kringle structures have been identified in various other proteins such as prothrombin, tissue-type plasminogen activator (t-PA), urokinase and coagulation factor XII (Utermann, SCIENCE, 246:904-910, 905 (1989)). Apo(a) lacks kringles similar to I to III of plasminogen but has multiple copies of the kringle domain similar to the fourth one of plasminogen, and a single copy of a kringle domain similar to the fifth one of plasminogen (kringle-5). Apo(a) also contains a protease domain.

Lp(a) was first identified by Berg in 1963 (Berg, ACTA PATHOL. MICROBIOL. SCAND., 59:369 (1963)) as an antigenic activity associated with the LDL fraction in the plasma of some individuals. Plasma Lp(a) levels vary in different individuals from less than 2 mg/dl to greater than 200 mg/dl. Increased plasma Lp(a) levels are considered to be a risk factor for atherosclerosis, either alone or in conjunction with elevated LDL levels (Kostner et al., CIRCULATION, 80(5):1313-1319 (1989) citing previous investigators). The plasma concentration of Lp(a) and the size of apo(a) are genetically determined (Gavish et al., J. CLIN. INVEST., 84:2021-2027 (1989)).

The discovery of the homology of apo(a) to plasminogen has prompted further investigation as to the role played by Lp(a). Hajjar et al. considered the similarity between the apo(a) component of Lp(a) and plasminogen and investigated the effect that Lp(a) might have on the interaction between plasminogen and the endothelial cell, and found that Lp(a) competed for plasminogen binding sites and appeared to be capable of inhibiting the activation of plasminogen on the surface of endothelial cells by t-PA. This suggests that elevated levels of Lp(a) might impair and inhibit cell surface fibrinolysis and thereby encourage the development of a more prothrombotic environment (Hajjar et al., NATURE, 339(6222):303-305 (1989). It is presently suspected that Lp(a) promotes atherogenesis by promoting thrombotic tendencies and interfering with the metabolism of LDL. These observations taken with the relationship between increased concentrations of Lp(a) and increased cardiovascular risk, have prompted the search for ways by which Lp(a) concentrations may be lowered.

Efforts to lower p(a) levels in plasma have included studies wherein known LDL lowering agents have been administered and observed. Thus, in Kostner et al., supra., HMG CoA Reductase inhibitors such as Simvastatin and Lovastatin as well as other known cholesterol-lowering agents were administered to a test group of patients and plasma samples thereafter were taken and examined. None of the tested agents appeared to lower Lp(a) levels, and, in fact, in some instances, Lp(a) levels appeared to rise, possibly due to stimulation of Lp(a) production. The authors identified only two agents, namely neomycin and niacin, that are known to decrease both LDL and Lp(a) levels. These agents only lower Lp(a) to a limited extent and because of this as well as toxic side effects do not appear to present a viable therapeutic avenue.

A need therefore exists for an effective method and associated agents for decreasing plasma Lp(a) levels.

SUMMARY OF THE INVENTION

In accordance with the present invention, a method and corresponding agents are disclosed for diminishing plasma Lp(a) levels, either by the selective reduction of Lp(a) and liberation of the apo(a) component thereof and/or blocking the association of apo(a) with LDL and preventing Lp(a) formation. The agents of the present invention appear to be capable of cleaving and/or preventing from forming the disulfide bond that extends between apo B and apo(a) without disturbing the disulfide bonds that are present in the kringle domains of apo(a) or any of the other blood or body proteins present in the host. The invention extends to agents that may possess either or both of the noted capabilities.

Suitable agents include sulphur-containing compounds, such as cysteine, N-acetylcysteine, diacetylcysteine, glutathione, dithiothreitol, ergothionine, 3-mercapto-D-valine, dimercaptopropanol, dimercaptopropane sulfonic acid, dimercaptosuccinic acid, as well as pharmaceutically acceptable analogs, pro-drugs thereof, and mixtures. A particularly preferred agent comprises N-acetylcysteine.

More particularly, the present invention comprises a composition for lowering Lp(a) plasma levels comprising the agent of the present invention in a pharmaceutically acceptable carrier. Pharmaceutical compositions containing the agents of the present invention may be prepared in a variety of forms for oral administration. For example, the agent may be prepared in an elixir with a concentration of the agent of up to about 20 percent. The elixir may then be administered together with water or a biocompatible soft drink to achieve the same dosage and periodicity.

The method of the present invention comprises the administration of the reducing agents in amounts therapeutically effective to lower Lp(a) plasma levels. More particularly, the present method comprises the periodic administration of quantities of the present agents in amounts of up to about 100 mg/kg/day. The present method and associated agents may be administered alone or in conjunction with known LDL- and/or cholesterol-lowering protocols.

The reduction of Lp(a) levels can be achieved in accordance with the present invention in a manner which is safe and effective. In the instance of the reducing agent N-acetylcysteine, this agent is known as a mucolytic and is presently administered in the instance of chronic lung disease and to treat overdoses of acetaminophen. It is a particularly safe medication that may confer substantial therapeutic benefit in the present instance.

While the exact function of Lp(a) is presently unknown, the ability to lower levels of Lp(a) is significant, owing to its observed resistance to traditional LDL-lowering protocols. The present invention therefore promises to offer advantages to the treatment of cardiovascular pathologies including those resulting in part from atherosclerosis. More generally, the present method and associated agents offer a means for the modulation of Lp(a) levels that promises to be of therapeutic significance.

Accordingly, it is a principal object of the present invention to provide an agent for reducing Lp(a) levels that does not cause unwanted side effects.

It is a further object of the present invention to provide an agent as aforesaid that is capable of selectively reducing the disulfide bond between the LDL component and the apo(a) component of Lp(a) and/or preventing this bond from forming.

It is a further object of the present invention to prepare therapeutic compositions containing the agents as aforesaid, which are capable of safe and extended administration.

It is a still further object of the present invention to provide therapeutic methods employing the agents of the present invention which may lower Lp(a) plasma levels.

It is a still further object of the present invention to provide therapeutic methods as aforesaid that may be administered in conjunction with protocols for the lowering of low density lipoproteins and/or cholesterol.

Other objects and advantages will become apparent from a consideration of the ensuing detailed description which proceeds with reference to the following illustrative drawings.

BRIEF DESCRIPTION OF THE DRAWINGS

FIGS. 1 and 2 are graphs depicting the lowering effect on the level of Lp(a) in two patients, respectively, resulting from the administration of an Lp(a) lowering agent in accordance with the invention.

DETAILED DESCRIPTION

Figure 1:
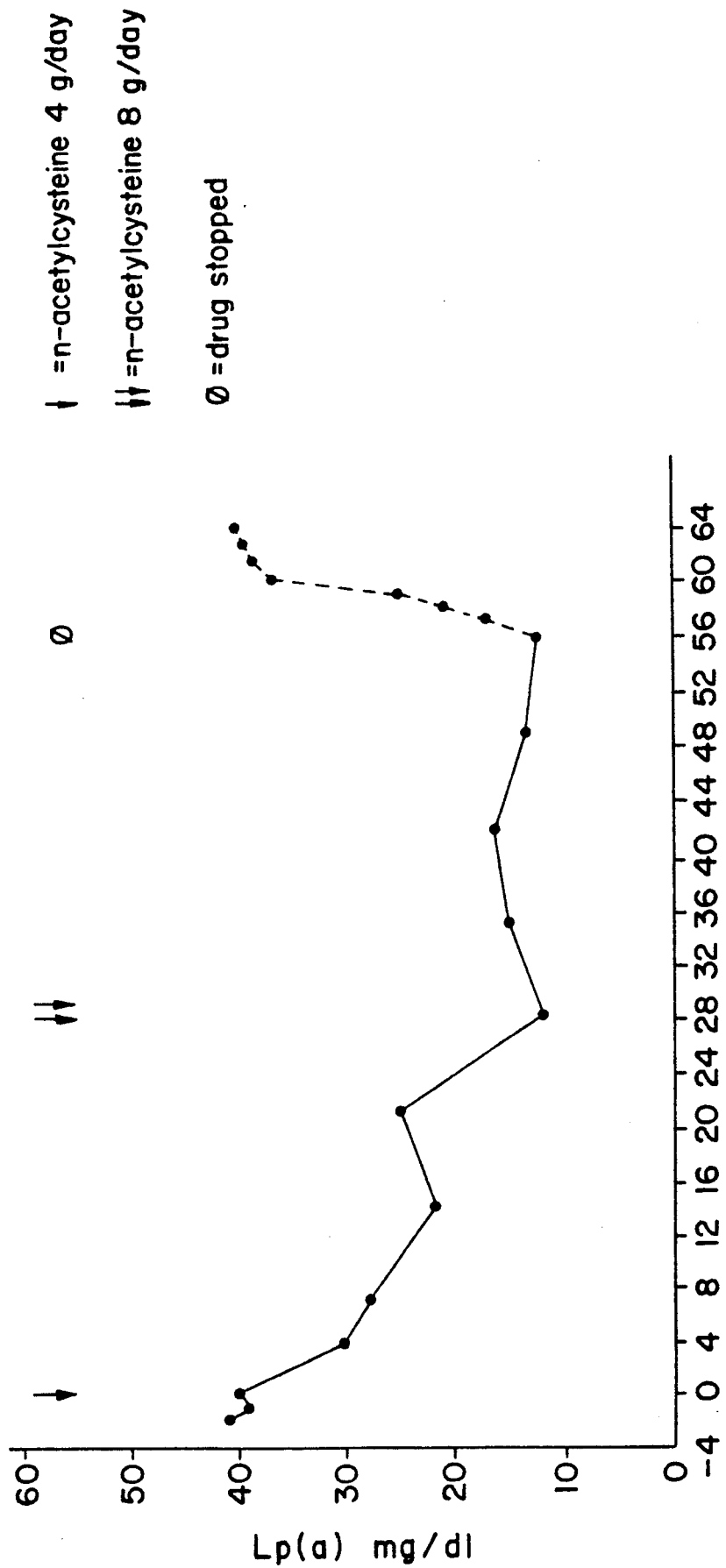

In accordance with the present invention, a method and associated agents are disclosed for the reduction of the level of Lp(a) in human plasma. The method of the invention comprises administering an agent or a pharmaceutical composition containing the agent that is capable of the selective reduction of Lp(a) to cleave the apo(a) component thereof and/or the prevention of formation of Lp(a), in an amount effective to lower the level of Lp(a). As noted earlier, the invention extends to agents that may possess either or both capabilities.

The term "selective reduction" as used herein refers to the cleavage of the bond between apo(a) and apo B that does not cause unwanted cleavage of the disulfide bonds found in the kringle domains present in other body proteins known to have such domains.

The bond that extends between apo B and apo(a) is a disulfide bond, and accordingly suitable agents include compounds and compositions that are capable of reducing such bonds to sulfhydryl groups, and that are also known as sulfhydryl reducing agents. However, the term "sulfhydryl reducing agent(s)" as used herein includes those agents capable of cleaving disulfide bonds but which result in the selective reduction of Lp(a) as defined above and/or the prevention of Lp(a) formation.

Suitable agents include sulphur-containing compounds, such as cysteine, N-acetylcysteine, diacetylcysteine, glutathione, dithiothreitol, ergothionine, 3-mercapto-D-valine, dimercaptopropanol, dimercaptopropane sulfonic acid, dimercaptosuccinic acid, as well as pharmaceutically acceptable analogs, pro-drugs thereof, and mixtures. Naturally, other biocompatible reducing agents capable of selectively diminishing Lp(a) levels are contemplated and included herein, and the foregoing list of agents should be considered illustrative rather than limitative.

A particularly preferred agent comprises N-acetyl cysteine, which is presently in use as a mucolytic agent, and is formulated and sold under the name MUCOMYST ® by Bristol Laboratories, Division of Bristol-Myers U.S. Pharmaceutical and Nutritional Group, Evansville, Ind. It is employed to decrease the viscosity of abnormal mucous secretions in conditions such as chronic bronchopulmonary disease. It is also used to prevent liver and kidney damage resulting from acetaminophen overdose. The agent may be prepared as a tablet, caplet, or capsule as a 20% solution, and usually includes minor amounts of certain inactive ingredients such as disodium edetate, sodium hydroxide and water.

Where appropriate or desirable, the present agents can be formulated into the therapeutic compositions as neutralized pharmaceutically acceptable salt forms. Pharmaceutically acceptable salts include the acid addition salts which are formed with inorganic acids such as, for example, hydrochloric or phosphoric acids, or such organic acids as acetic, oxalic, tartaric, mandelic, and the like. Salts formed from any free carboxyl or like groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

More particularly, the present invention comprises a pharmaceutical composition for lowering Lp(a) plasma levels comprising a therapeutically effective amount of the agent of the present invention and a pharmaceutically acceptable carrier. Concentrates containing the agent may be prepared which may then be administered directly, or diluted or co-administered with a suitable liquid such as water or a biocompatible soft drink.

The active therapeutic ingredient is often mixed with excipients which are pharmaceutically acceptable and compatible with the active ingredient. Suitable excipients are, for example, water, saline, dextrose, or the like, and combinations thereof. The agent may be prepared in an elixir or with a soft drink or other like preparation. Likewise, the agent may be formulated as a hard or soft candy or in a chewing gum, or other like comestible. In addition, if desired, the composition can contain minor amounts of auxiliary substances such as wetting or emulsifying agents and pH buffering agents, which enhance the effectiveness of the active ingredient.

The present compositions may be conventionally administered orally, as, for example, by ingestion of a unit dose. The term "unit dose" when used in reference to a therapeutic composition of the present invention refers to physically discrete units suitable as unitary dosage for humans, each unit containing a predetermined quantity of active material calculated to produce the desired therapeutic effect in association with the required diluent; i.e., carrier, or vehicle.

The compositions are administered in a manner compatible with the dosage formulation, and in a therapeutically effective amount. The quantity to be administered depends on the subject to be treated, quantity of Lp(a) present in the subject's system for which reduction is desired and amount reduction of Lp(a) concentration desired. Precise amounts of active ingredient required to be administered depend on the judgment of the practitioner and are peculiar to each individual. However, suitable dosage ranges are of the order of about 1 to about 100, preferably about 1 to about 50, and more preferably from about 25 to about 50 milligrams of active ingredient per kilogram body weight of individual per day. Suitable regimes for administration are also variable, but are typified by a daily regimen of administration by repeated doses given either once or twice daily, or at one or more hourly intervals.

In an alternative embodiment, the invention includes the co-administration of the present reducing agents as part of a therapeutic protocol for lowering both Lp(a) and LDL cholesterol levels. Thus, the present reducing agents may be co-administered with conventional LDL cholesterol-lowering agents such as Lovastatin, cholestyramine and the like, to effect the conjoint reduction in the concentrations and levels of LDL and Lp(a).

While the present invention is described and illustrated with respect to humans, it is to be understood that it is applicable to other mammals wherein Lp(a) is present and it is or may be desirable to modulate Lp(a) levels. Accordingly, where used herein in the Specification and Claims, the term "humans" is intended to be inclusive of mammals in which Lp(a) is present and the modulation of Lp(a) levels in the body may be desirable.

The present invention will now be better appreciated from a review of the following illustrative examples comprising both in vitro and in vivo experiments.

EXAMPLE 1

Blood samples were taken from patients, and plasma was thereafter separated. The resulting plasma samples were further prepared by the addition of preservatives and were then subjected to separation to recover the Lp(a) fractions thereof. Four aliquot portions of the Lp(a) fraction were then incubated at 37° C. for a period of up to three hours, With samples taken and observed at four intervals. Three of the samples were incubated with potential reducing agents, including dithiothreitol (DTT), β-mercaptoethanol, and a preparation including MUCOMYST ® (N-acetylcysteine). A fourth sample comprising a control was likewise prepared.

Each of the samples was subsequently subjected to immunoblot analysis to determine the extent to which the reducing agents caused the cleavage of Lp(a) and the liberation of apo(a). The samples were subjected to SDS-PAGE, and the results thereof revealed that N-acetylcysteine was effective in reducing Lp(a) even in concentrations of 1:100 of a 10 percent solution. These data indicated that the reduction of Lp(a) by N-acetylcysteine was accomplished on an in vitro basis, and that further experimentation, including clinical in vivo testing was warranted.

EXAMPLE 2

Based upon the successful completion of the in vitro experiment set forth in Example 1, a clinical experiment with two patients was conducted. The subjects were chosen from the clinic population of the Rockefeller University Hospital. Accordingly, the patients were first screened for high levels of Lp(a) (>40 mg/dl), and a protocol developed for the administration of a suitable solution of N-acetylcysteine.

Subjects known to suffer from asthma or on drugs with low therapeutic indices which require oxidative metabolism (e.g., theophylline, warfarin) were excluded from the study. Women of childbearing age were excluded from the study. A baseline total bilirubin, SGOT, SGPT or serum creatinine that is more than 30% above the normal range for the laboratory performing the test has a reason for exclusion from the study.

A full physical examination was done prior to the study and after every period of study. Toxicity screening which included a cpk, alkaline phosphatase, SGOT SGPT, creatinine, total bilirubin, CBC with differential, platelet count and prothrombin time, partial thromboplastin time, serum uric acid and electrolytes, was followed once a week.

During these periods the subjects were maintained on an in-patient basis on a constant diet. Each subject was placed on a regimen of administration of N-acetylcysteine in accordance with the following protocol: from Week No. 1 through Week No. 4, each patient was given 10 ml of a 20% solution of MUCOMYST ® mixed with a diet soda twice daily, equivalent to 4 grams of the agent per day, at 8:00 a.m. and 6:00 p.m.; from Week No. 5 through Week No. 8, each patient was given 20 ml of a 20% solution of MUCOMYST ® twice daily and equivalent to 8 grams of the agent per day, in the same manner as previously; and, after Week No. 8, administration was terminated.

During this study, the subjects underwent monitoring of lipid and lipoprotein levels, Lp(a) levels and toxicity (defined above). Blood was drawn three times a week for lipoprotein and Lp(a) levels, and once a week for toxicity screening. A single amount of 100 ml was drawn prior to the study and at the end of each study period for preparation of Lp(a) that was used for in vitro and tissue culture assays. No other medications were taken by the subjects three months prior and throughout the study.

The gross data gathered in this study from each of the patients is separately presented in Tables I and II, below. Lp(a) levels of each patient presented in Tables I and II have been plotted against time and are presented in FIGS. 1 and 2, respectively.

In both the Tables and the Figures, the symbol "↓" denotes the commencement of the administration of the first lower dose of N-acetylcysteine, the symbol "↓ ↓" identifies the commencement of the administration of the second higher dose of N-acetylcysteine, and the symbol "φ" identifies the termination of administration.

TABLE I

SUBJECT NO. 1

| | Baseline | 1st Wk. ↓ | 2nd Wk. | 3rd Wk. | 4th Wk. | 5th Wk. ↓↓ | 6th Wk. | 7th Wk. | 8th Wk. | 9th Wk. φ | 12th Wk. |
|---|---|---|---|---|---|---|---|---|---|---|---|
| Total Cholesterol | 452 | 474 | 424 | 449 | 463 | 473 | 483 | 474 | 432 | 430 | 430 |
| Total TG | 219 | 186 | 186 | 165 | 235 | 178 | 179 | 247 | 145 | 125 | 130 |
| VLDL-C | 38 | 17 | 21 | 35 | 40 | 37 | 42 | 60 | 21 | 12 | 14 |
| LDL-C | 386 | 425 | 369 | 384 | 394 | 412 | 409 | 387 | 379 | 386 | 380 |
| HDL-C | 28 | 32 | 34 | 30 | 29 | 24 | 32 | 27 | 32 | 32 | 36 |
| Lp(a) | 42 | 31 | 28 | 23 | 25 | 12 | 15 | 18 | 13 | 38 | 42 |
| PT (sec) (<13.1) | 12.2 | | 12.1 | | 12.0 | | 12.2 | | 12.4 | | |
| PTT (sec) (<38.1) | 35 | | 32.5 | | 37.4 | | 34.6 | | 33.9 | | |
| Hgb | 13.5 | 14.2 | | 13.9 | 15.2 | | 14.3 | | 14.3 | 13.7 | |
| WBC | 6800 | 7100 | | 5500 | 8700 | | 8100 | | 6500 | 8300 | |
| PLT × 10³ | 182 | 171 | | 165 | 192 | | 185 | | 176 | 171 | |
| Glucose | 116 | 104 | | 110 | 97 | | 101 | | 110 | 86 | |
| Urea | 14 | 20 | | 18 | 15 | | 15 | | 12 | 12 | |
| Creatinine | 1.0 | 1.0 | | 1.1 | 0.9 | | 1.1 | | 1.0 | 0.9 | |
| CPK | 150 | 122 | | 130 | 115 | | 146 | | 81 | 80 | |
| LDH | 155 | 140 | | 152 | 141 | | 130 | | 134 | 135 | |
| GOT | 24 | 26 | | 26 | 22 | | 20 | | 20 | 22 | |
| GPT | 18 | 20 | | 19 | 22 | | 20 | | 19 | 20 | |
| Alk. Phos. | 86 | 83 | | 83 | 103 | | 94 | | 102 | 93 | |
| Uric Acid | 8.4 | 8.7 | | 8.5 | 7.6 | | 8.1 | | 8.3 | 8.0 | |
| Albumin | 4.1 | 4.3 | | 4.2 | 4.5 | | 4.6 | | 4.5 | 4.3 | |
| Total Protein | 6.3 | 6.8 | | 6.4 | 7.1 | | 7.1 | | 7.2 | 6.9 | |
| Protein | — | — | — | — | — | | — | — | — | — | — |
| Crystals | — | — | — | — | — | | — | — | — | — | — |
| pH | 5.0 | 5.5 | 5.0 | 5.0 | 5.5 | 5.0 | 5.0 | 5.0 | 5.0 | 5.0 | |

TABLE II

SUBJECT NO. 2

| | Baseline | 1st Wk. ↓ | 2nd Wk. | 3rd Wk. | 4th Wk. | 5th Wk. ↓↓ | 6th Wk. | 7th Wk. | 8th Wk. | 9th Wk. φ | 12th Wk. |
|---|---|---|---|---|---|---|---|---|---|---|---|
| Total Cholesterol | 203 | 199 | 214 | 209 | 200 | 189 | 223 | 218 | 221 | 203 | |
| Total TG | 82 | 111 | 82 | 104 | 79 | 96 | 127 | 96 | 74 | 84 | |
| VLDL-C | 15 | 17 | 11 | 20 | 18 | 18 | 23 | 16 | 22 | 16 | |
| LDL-C | 130 | 129 | 143 | 137 | 130 | 119 | 142 | 144 | 139 | 119 | |
| HDL-C | 58 | 53 | 60 | 52 | 52 | 52 | 58 | 58 | 60 | 56 | |
| Lp(a) | 59 | 58 | 47 | 30 | 23 | 19 | 16 | 13 | 13 | 57 | |
| PT (sec) (<13.1) | 12.2 | | 12.3 | | 12.0 | | 12 | | 12.3 | | |
| PTT (sec) (<38.1) | 32 | | 31.8 | | 32.8 | | 28 | | 29.7 | | |
| Hgb | 14.1 | | | | 13.5 | | 13.6 | | 13.9 | 14 | |
| WBC | 4600 | | 3200 | | 3300 | | 4600 | | 3700 | 4000 | |
| PLT × 10³ | 252 | | 255 | | 254 | | 254 | | 262 | 255 | |
| Glucose | 83 | | 76 | | 86 | | 74 | | 91 | 81 | |
| Urea | 13 | | 14 | | 12 | | 11 | | 13 | 13 | |
| Creatinine | 1.1 | | 1.1 | | 1.0 | | 1.0 | | 1.0 | 1.1 | |
| CPK | 67 | | 78 | | 67 | | 85 | | 67 | 55 | |
| LDH | 142 | | 143 | | 131 | | 131 | | 130 | 124 | |
| GOT | 35 | | 37 | | 33 | | 39 | | 37 | 30 | |
| GPT | 17 | | 18 | | 15 | | 19 | | 18 | 16 | |
| Alk. Phos. | 82 | | 80 | | 73 | | 70 | | 71 | 73 | |
| Uric Acid | 5.6 | | 5.3 | | 4.7 | | 4.0 | | 4.6 | 4.8 | |
| Albumin | 4.9 | | 4.5 | | 4.3 | | 4.6 | | 4.6 | 4.7 | |
| Total Protein | 7.0 | | 6.2 | | 6.2 | | 6.4 | | 6.3 | 6.5 | |
| Protein | — | — | — | — | — | | — | — | — | — | |
| Crystals | — | — | — | — | — | | — | — | — | — | |
| pH | 5.0 | | 5.0 | | 5.0 | | 5.0 | 5.5 | 5.0 | 5.0 | |

Referring to both the Tables and the Figures, blood analysis from the subjects revealed that N-acetylcysteine successfully lowered Lp(a) concentrations 70%. This was apparent after three weeks of drug treatment with values remaining at the reduced level during an ensuing five weeks of continued therapy. Following the termination of administration of N-acetylcysteine, the concentration of Lp(a) increased to pretreatment levels within 4-6 days. During the entire period that the present study was conducted, the subjects were observed and no adverse side effects were noted.

This invention may be embodied in other forms or carried out in other ways without departing from the spirit or essential characteristics thereof. The present disclosure is therefore to be considered as in all respects illustrative and not restrictive, the scope of the invention being indicated by the appended claims, and all changes which come within the meaning and range of equivalency are intended to be embraced therein.

What is claimed is:

1. A method for lowering the serum or plasma level of Lp(a) in a mammal in need of such treatment, comprising administering to said mammal an agent or a pharmaceutical composition containing said agent in an amount effective for lowering the serum or plasma level of said Lp(a), wherein said agent has at least one of the following abilities to thereby lower the serum or plasma level of Lp(a):
(a) the ability to selectively reduce Lp(a) to cleave the apo (a) component therefrom; and
(b) the ability to prevent Lp(a) formation; and wherein the agent or pharmaceutical composition administered is effective for lowering the serum or plasma Lp(a) level without causing the unwanted cleavage of disulfide bonds found in the kringle domains of other body proteins, or substantially affecting the serum or plasma LDL cholesterol level in said mammal.

2. The method of claim 1, wherein said agent possesses both of said abilities.

3. The method of claim 1, wherein said agent comprises a sulfhydryl reducing agent.

4. The method of claim 1, wherein said agent is selected from the group consisting of diacetylcysteine, dithiothreitol, ergothionine, 3-mercapto-D-valine, dimercaptopropanol, dimercaptopropane sulfonic acid, dimercaptosuccinic acid, and mixtures thereof.

5. The method of claim 4, wherein said agent is selected from the pharmaceutically acceptable salts of said compounds, and mixtures thereof.

6. The method of claim 4, wherein said agent is selected from the pharmaceutically acceptable pro-drugs of said compounds, the salts thereof, and mixtures thereof.

7. The method of claim 1, wherein a composition is administered in the form of a solution having a concentration of said agent of up to about 20 percent by weight.

8. The method of claim 7 wherein said solution is prepared as an elixir.

9. The method of claim 1, wherein said composition is administered in the form of a soft drink.

10. The method of claim 1, wherein said composition is administered in the form of a hard candy.

11. The method of claim 1, wherein said composition is administered in the form of a soft candy.

12. The method of claim 1, wherein said composition is administered in the form of chewing gum.

13. The method of claim 1, wherein said composition is administered orally.

14. The method of claim 1, wherein said composition is administered at least once daily and at a concentration of said agent of up to about 100 mg/kg of body weight.

15. The method of claim 1, wherein said composition is administered to deliver said agent in an amount ranging from about 25 to about 50 mg/kg of body weight per day.

16. The method of claim 1, wherein said composition is administered to deliver said agent in an amount ranging from about 40 to about 50 mg/kg of body weight per day.

17. The method of claim 1, wherein said composition is administered in conjunction with another therapeutic agent administered in an amount effective for lowering serum or plasma LDL cholesterol levels.

18. A method of lowering the level of serum or plasma Lp(a) in a mammal comprising administering to said mammal a serum or plasma level Lp(a)-lowering effective amount of N-acetylcysteine.

19. A method in accordance with claim 18 wherein the N-acetylcysteine is administered in an amount ranging from about 1 to about 100 mgs. per kg. body weight per day.

20. A method for lowering the serum or plasma Lp(a) level in a mammal in need of such treatment comprising administering to said mammal at least one agent selected from the group consisting of cysteine, glutathione and pharmaceutically acceptable salts thereof, in an amount effective for lowering the serum or plasma Lp(a) level in said mammal, wherein the agent administered is effective for lowering the serum or plasma Lp(a) level without causing the unwanted cleavage of disulfide bonds found in the kringle domains of other body proteins, or substantially affecting the serum or plasma LDL cholesterol level in said mammal.

21. A method in accordance with any of claim 4, 18 or 20, wherein the agent is administered orally, parenterally or via inhalation.

22. A method in accordance with either of claims 18 or 20, wherein the agent is administered orally in the form of a tablet, capsule, suspension, syrup, soft drink, hard candy, soft candy or chewing gum.

23. A method in accordance with either of claims 18 or 20, wherein the agent is administered parenterally in the form of an injectable solution, suspension or emulsion.

24. A method in accordance with either of claims 18 or 20, wherein the agent is administered via inhalation in the form of a powder, aerosol or solution.

* * * * *